(12) United States Patent
Smith et al.

(10) Patent No.: US 6,967,325 B2
(45) Date of Patent: Nov. 22, 2005

(54) HIGH PERFORMANCE ION MOBILITY SPECTROMETRY USING HOURGLASS ELECTRODYNAMIC FUNNEL AND INTERNAL ION FUNNEL

(75) Inventors: Richard D. Smith, Richland, WA (US); Keqi Tang, Richland, WA (US); Alexandre A. Shvartsburg, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/933,661

(22) Filed: Sep. 2, 2004

(65) Prior Publication Data
US 2005/0092918 A1 May 5, 2005

Related U.S. Application Data

(63) Continuation-in-part of application No. 10/699,006, filed on Oct. 30, 2003, now Pat. No. 6,818,890.

(51) Int. Cl.$^7$ ............................................. H01J 49/04
(52) U.S. Cl. ..................... 250/288; 250/290; 250/291; 250/292; 250/396 R
(58) Field of Search ....................... 250/288, 290–292, 250/396 R (56) References Cited

U.S. PATENT DOCUMENTS 6,670,606 B2 * 12/2003 Verentchikov et al. ...... 250/287

* cited by examiner

Primary Examiner—Nikita Wells
Assistant Examiner—Zia R. Hashmi
(74) Attorney, Agent, or Firm—Todd J. Harrington (57) ABSTRACT

A method and apparatus enabling increased sensitivity in ion mobility spectrometry/mass spectrometry instruments which substantially reduces or eliminates the loss of ions in ion mobility spectrometer drift tubes utilizing a device for transmitting ions from an ion source which allows the transmission of ions without significant delay to an hourglass electrodynamic ion funnel at the entrance to the drift tube and/or an internal ion funnel at the exit of the drift tube. An hourglass electrodynamic funnel is formed of at least an entry element, a center element, and an exit element, wherein the aperture of the center element is smaller than the aperture of the entry element and the aperture of the exit elements. Ions generated in a relatively high pressure region by an ion source at the exterior of the hourglass electrodynamic funnel are transmitted to a relatively low pressure region at the entrance of the hourglass funnel through a conductance limiting orifice. Alternating and direct electrical potentials are applied to the elements of the hourglass electrodynamic funnel thereby drawing ions into and through the hourglass electrodynamic funnel thereby introducing relatively large quantities of ions into the drift tube while maintaining the gas pressure and composition at the interior of the drift tube as distinct from those at the entrance of the electrodynamic funnel and allowing a positive gas pressure to be maintained within the drift tube, if desired. An internal ion funnel is provided within the drift tube and is positioned at the exit of said drift tube. The advantage of the internal ion funnel is that ions that are dispersed away from the exit aperture within the drift tube, such as those that are typically lost in conventional drift tubes to any subsequent analysis or measurement, are instead directed through the exit of the drift tube, vastly increasing the amount of ions exiting the drift tube.

104 Claims, 10 Drawing Sheets

HIGH PERFORMANCE ION MOBILITY SPECTROMETRY USING HOURGLASS ELECTRODYNAMIC FUNNEL AND INTERNAL ION FUNNEL

This application is a Continuation-In-Part of U.S. application Ser. No. 10/699,006 filed Oct. 30, 2003, now U.S. Pat. No. 6,818,890.

STATEMENT REGARDING FEDERALLY SPONSORED RESEARCH OR DEVELOPMENT

This invention was made with Government support under Contract DE-AC0676RLO1830 awarded by the U.S. Department of Energy. The Government has certain rights in the invention.

BACKGROUND OF THE INVENTION

The hope of achieving high performance identification of ionic species using ion mobility drift tubes coupled with time of flight mass spectrometers has long been held by those skilled in the art. The general concept has been known since at least the publication of the paper entitled "Ion Mobility/Mass Spectrometric Investigation of Electrospray Ions" by R. Guevremont, K. W. M. Siu, and L. Ding in the Proceedings of the 44th ASMS Conference, p. 1090 (1996). This paper, and all other papers and patents identified herein are hereby explicitly incorporated into this disclosure by this reference. The concept was again published in the paper "Combined ion mobility/time-of-flight mass spectrometry study of electrospray-generated ions. Anal. Chem. 69, 3959 (1997). The concept was again described in the patent literature in May of 1999, when U.S. Pat. No. 5,905,258 titled "Hybrid ion mobility and mass spectrometer" issued to David E. Clemmer, et al.

While the general concept of such systems has thus long been recognized, those having skill in the art have also recognized limitations associated with the technique when put into practice. One approach towards achieving the objective of increased sensitivity in ion mobility spectrometry/mass spectrometry (IMS/MS) instruments is described in U.S. Patent Application Pub No. 2001/0032929A1 by Fuhrer et al. wherein improvements in sensitivity are claimed as a result of preserving a narrow spatial distribution of migrating ions through the use of periodic/hyperbolic field focusing. Variations on the general IMS/MS concept are shown in U.S. Pat. No. 6,323,482 filed May 17, 1999, granted Nov. 27, 2001, "Ion mobility and mass spectrometer" which shows the use of collision cell in an IMS/time of flight MS hybrid system and various means to incorporate the collision cell into such instrumentation. Further variations are also shown in U.S. Pat. No. 6,498,342 filed Jul. 13, 2000, granted Dec. 24, 2002 "Ion separation instrument" which introduces the liquid-phase separation (such as liquid chromatography) prior to IMS/time of flight MS or a tandem IMS/time of flight MS system. Finally, U.S. Pat. No. 6,559,441 filed Feb. 12, 2002, granted May 6, 2003 "Ion separation instrument" details various conceivable versions of tandem IMS, e.g. use of different buffer gases and/or different temperatures.

Despite these and other improvements, problems associated with loss of ions in ion mobility spectrometer (IMS) drift tubes have continued to prevent IMS/MS systems from reaching their full potential as analytical instruments. Rather, other systems with much slower separations times, but lower ion losses, such as liquid chromatography mass spectrometry (LC/MS), have prevailed despite the sample analysis "throughput" reductions associated with such systems. The problem of excessive ion losses in IMS/MS systems is well known by those having skill in the art, and has repeatedly been identified in the literature by numerous researchers active in the field. For example, in the paper titled "Gas-phase separations of complex tryptic peptide mixtures" published in Fresenius J. Anal. Chem. 369, 234 (2001), by J. A. Taraszka, A. E. Counterman and D. E. Clemmer, in the sentence bridging pages 242 and 243, the authors described one aspect of the problem thusly: "Currently one stumbling block associated with high-resolution instruments is that most signal (~99–99.9%) is discarded when the short pulse of ions is introduced into the drift tube." In the paper titled "Multidimensional separations of complex peptide mixtures: a combined high performance liquid chromatography/ion mobility/time-of-flight mass spectrometry approach" published in Intern. J. Mass Spectrom. 212, 97 (2001), by S. J. Valentine, M. Kulchania, C. A. Srebalus Barnes, and D. E. Clemmer, at the final paragraph on page 108, the authors again recognize difficulties with the technique stating: "It is typical to discard 99–99.9% of the ion signal during the mobility experiment [34]; thus, these experiments are inherently less sensitive than conventional LC-ESI-MS methods." Yet another paper in the literature identifying the problem is entitled "Coupling ion mobility separations, collisional activation techniques, and multipole stages of MS for analysis of complex peptide mixtures", Anal. Chem. 74, 992 (2002), by C. S. Hoaglund-Hyzer, Y. J. Lee, A. E. Counterman, and D. E. Clemmer. At page 1005, the authors state: "We also note that although improvements in sensitivity have been demonstrated, the current technologies are still not as sensitive as the well-developed MS/MS strategies; however we believe that much of this difference will be diminished as additional improvements in the instruments are made. Finally, other authors, including Russell and coworkers active in the field at Texas A&M University, have repeatedly pointed out the need for much better IMS/MS sensitivity.

Thus, there remains a need for methods and apparatus that enable increased sensitivity in ion mobility spectrometry/mass spectrometry (IMS/MS) instruments and which substantially reduces the loss of ions in ion mobility spectrometer (IMS) drift tubes.

BRIEF SUMMARY OF THE INVENTION

Accordingly, it is an object of the present invention to provide methods and apparatus that enable increased sensitivity in ion mobility spectrometry/mass spectrometry instruments and substantially reduce the loss of ions in ion mobility spectrometer drift tubes. These and other objects of the present invention are accomplished by providing a method and apparatus for analyzing ions utilizing an hourglass electrodynamic ion funnel at the entrance to the drift tube and/or an ion funnel at the exit of the drift tube, as shown in the cutaway schematic drawing of FIG. 1. Briefly, the present invention comprises an hourglass electrodynamic funnel 1 formed of at least an entry element 2, a center element 3, and an exit element 4, each of said elements having an aperture. The entry element 2 is aligned such that a passageway for charged particles is formed through the aperture within the entry element 2, through an aperture in the center element 3, and then through the aperture in the exit element 4. It is important that the aperture in the center element 3 is smaller than the aperture of the entry element 2 and the aperture of the exit element 4. Typically, the hourglass electrodynamic funnel 1 will consist of more than three elements, perhaps as many as several hundred elements. It is not necessary that the center element 3 be at the exact middle of all elements. In an embodiment, for example, with 100 elements, the center element 3 could be the 80$^{th}$ element, rendering the electrodynamic funnel asymmetric. All that is required of the center element 3 is that it be the smallest of the elements, and that the center element 3 have at least one element (the entry 2 and exit element 4) to each of both sides. Conceptually, therefore, three elements are the minimum necessary to describe and operate the invention.

Figure 1:
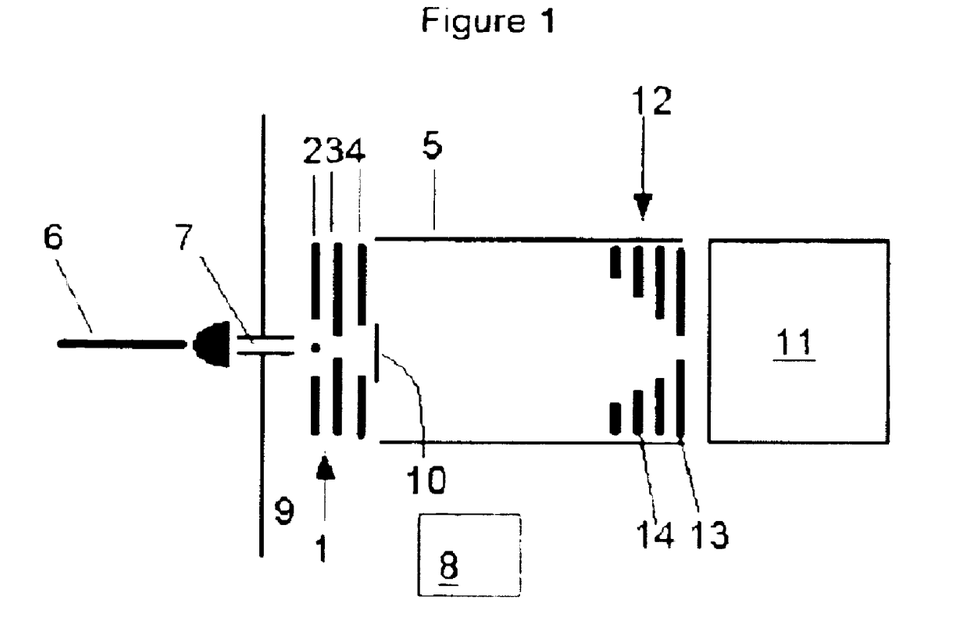
FIG. 1 is a schematic cut away drawing of the present invention.

The hourglass electrodynamic funnel 1 forms the entrance to a drift tube 5. Ions generated in a relatively high pressure region by an ion source 6 at the exterior of the hourglass electrodynamic funnel 1 are transmitted to a relatively low pressure region at the entrance of the hourglass funnel 1 through a conductance limiting orifice 7, which may be fashioned from, by way of example, a heated capillary. Typically, a differential pump 8 evacuates the hourglass electrodynamic funnel chamber. Alternating and direct electrical potentials are applied to the elements of the hourglass electrodynamic funnel 1 as with a standard ion funnel as described in U.S. Pat. No. 6,107,628, issued Aug. 22, 2000, and entitled "Method and apparatus for directing ions and other charged particles generated at near atmospheric pressures into a region under vacuum" the entire contents of which are hereby incorporated herein by this reference, thereby drawing ions into and through the hourglass electrodynamic funnel 1. In this manner, the hourglass electrodynamic funnel 1 captures an expanding flow of ions generated in a relatively high pressure region and directs them through the small aperture of the center element 3, into the drift tube 5 which is maintained at a relatively low pressure compared to the ion generation region. The center element 3 thus defines a small aperture for the entry to the drift tube 5, and thus a conductance limit. Combined with the entry element 2, this configuration introduces relatively large quantities of ions into the drift tube 5 while maintaining the gas pressure and composition at the interior of the drift tube 5 as distinct from those at the entrance of the electrodynamic funnel 1 and allowing a positive gas pressure to be maintained within the drift tube, if desired.

The electrodynamic funnel 1 may also utilize a jet disturber 9, such as that described in U.S. Pat. No. 6,583,408, issued Jun. 24, 2003 and entitled "Ionization source utilizing a jet disturber in combination with an ion funnel and method of operation" the entire contents of which are incorporated herein by this reference. The jet disturber 9 can be operated to prevent undesired species from entering the drift tube 5, to modulate the signal intensity, and to improve the signal to noise ratio. Additionally, the hourglass electrodynamic 1 funnel can include a further means 10 for temporarily containing the flow of ions out of the aperture of the exit element. These means could be a plurality of wires, a mesh, or a microchannel plate. Ions can be accumulated in the region between the center element 3 and the exit element 4, and by varying the potential applied to these means, pulsed through the exit element 4 at a known time, thereby allowing precise analysis of the time necessary for differing ions to pass through the flow tube. The hourglass shape of the electrodynamic funnel 1 thus allows the accumulation of much larger numbers of ions than is enabled by the conventional geometry of prior art ion funnels.

Alternatively, ions passing through electrodynamic funnel 1 may be pulsed by intermittent deflection by an electric field orthogonal to the ion path, generated by any of several means 10 known in the art, including, but not limited to, a Bradbury-Nielsen gate, two or more deflection plates, or a split lens.

While the apertures are typically circular, they may be any shape. For specific applications, for example to form ion packets having an elongated profile, and particularly a highly elongated "razor" profile, as is useful for field asymmetric waveform ion mobility spectrometry, photodissociation, and laser spectroscopy, ellipsoidal and rectangular apertures are preferred.

The exit of the drift tube 5, located at the opposite end of the drift tube from the hourglass electrodynamic funnel 1, is typically in communication with an ion analysis means 11, such as a mass spectrometer. While not meant to be limiting, the method and apparatus of the present invention can be in communication with a quadrupole mass spectrometer, a time of flight mass spectrometer, a Fourier-transform ion cyclotron resonance mass spectrometer, a photoelectron spectrometer, or a photodissociation spectrometer. The drift tube 5 can be an ion mobility spectrometer, a field asymmetric waveform ion mobility spectrometer, a selected ion flow tube, or a proton-transfer reaction mass spectrometer.

The present invention is capable of being interfaced with any conventional ion source 6, including but not limited to electrospray ionization, coldspray ionization, thermospray ionization, matrix-assisted laser desorption ionization, surface-enhanced laser desorption ionization, laser vaporization, and arc discharge.

The present invention may also be configured as having two or more hourglass electrodynamic funnels 1 each forming a separate entrance to the drift tube 5 thereby providing two or more passageways for ions generated in a relatively high pressure region at the exterior of the drift tube 5 to a relatively low pressure region at the interior of the drift tube 5. In this manner, the ease of calibration of the present invention is enhanced.

The present invention may also be configured as a dual entry hourglass electrodynamic funnel as described in U.S. patent application Ser. No. 10/400,356, filed Mar. 25, 2003, and entitled "Multi-Source Ion Funnel," the entire contents of which are incorporated herein by this reference. As shown in the Multi-Source Ion Funnel patent application, the dual source ion funnel is formed of at least two entry elements, one center element, and one exit element, each of the elements having an aperture, and wherein each of the two or more entry elements are aligned such that a passageway for charged particles is formed through apertures within the entry elements, through an aperture in said center element, and through the aperture in the exit element, thereby providing two separate but merging passageways for ions generated in a relatively high pressure region to a relatively low pressure region. As adapted for the present invention, as with the more general case, the aperture of the exit element 5 of the dual source configuration is again larger than each of the apertures of each of the center elements 3, and the two separate but merging passageways are for ions generated in a relatively high pressure region at the exterior of a drift tube 5 to the relatively low pressure region at the interior of the drift tube 5.

In another aspect of the present invention, an internal ion funnel 12 is provided within the drift tube 5. The internal ion funnel 12 is configured as a standard ion funnel; it has at least one element 13 having a relatively small aperture and at least one element having a relatively large aperture 14. Alternating and direct electrical potentials are applied to the elements of the internal ion funnel 12 as with a standard ion funnel as described in "Method and apparatus for directing ions and other charged particles generated at near atmospheric pressures into a region under vacuum," U.S. Pat. No.

6,107,628, issued Aug. 22, 2000. As with the hourglass electrodynamic funnel 1, the internal ion funnel 12 will typically consist of more than two elements, perhaps as many as 100 elements. Conceptually, however, as is the case with the standard ion funnel, two elements are the minimum necessary to operate internal ion funnel 12. The internal ion funnel 12 is positioned at the exit of said drift tube 5 wherein the element having the small aperture 13 is positioned adjacent to the exit of drift tube 5. The internal ion funnel 12 may be used alone or in combination with any of the aforementioned variations of the hourglass electrodynamic funnel 1. The advantage of the internal ion funnel 12 is that ions that are usually dispersed away from the exit aperture within the drift tube 5, such as those that are typically lost in conventional drift tubes to any subsequent analysis or measurement, are instead focused through the exit of the drift tube 5, vastly increasing the amount of ions exiting the drift tube 5.

While the general characteristics of the present invention have been shown and described, the operation and advantages of the present invention are best illustrated by an example. Accordingly, experiments in which the present invention was reduced to practice and then operated to demonstrate the superior performance enabled by the present invention when compared to prior art methods were conducted and are described below. However, the present invention should in no way be viewed as limited to either the specific device, or the operation of that device, as described below. Rather, these experiments are provided merely to illustrate the advantages of the present invention, and to illustrate an example of how the present may be reduced to practice and operated. Those having skill in the art will readily recognize that numerous departures from the specific details of the device and its operation shown below are possible, yet would still fall well within the more general description provided above, and set forth in the appended claims.

DETAILED DESCRIPTION OF THE INVENTION

A device was constructed to demonstrate the advantages and application of the present invention consisting of three sections: an ion source, and ion mobility spectrometer (IMS) drift tube for spatial ion separation, and a mass spectrometer for mass analysis of separated ion packets. Except as noted below, the device utilized the general arrangement of each of these components as shown in the conceptual drawing shown in FIG. 1. While all voltages listed below are for positively charged ions (cations), those having skill in the art will readily recognize that the polarities can readily be inverted to analyze negatively charged ions (anions).

This ion source section comprises an electrospray ionization (ESI) source that generates solvated ions, a heated capillary that desolvates them, and an hourglass electrodynamic (ED) ion funnel that further desolvates and focuses them into IMS. The ESI and the heated capillary were standard instruments available commercially from Waters/Micromass, Finnegan, and other mass spectrometer (MS) equipment manufacturers.

In the operation of the device, an ESI needle delivered the analyte solution pumped by a syringe pump through a capillary. Ions generated in ESI were sampled into a heated capillary with the internal diameter of ~0.5 mm and length of ~10 cm. To desolvate ions by thermal heating, this capillary was kept at ~120° C. by resistive heaters under a closed-loop control using a thermocouple.

Ions exiting the capillary were sampled into an hourglass ED funnel. Like a regular ion funnel in the prior art, the hourglass ED funnel consists of a stack of ~100 metal plates alternating with plastic plates for insulation and precise spacing, both plates ~0.5 mm. thick for the total funnel length of ~10 cm. Each plate has a round hole in the center, with the i.d varying between 25 mm and 2 mm.

Figure 2:
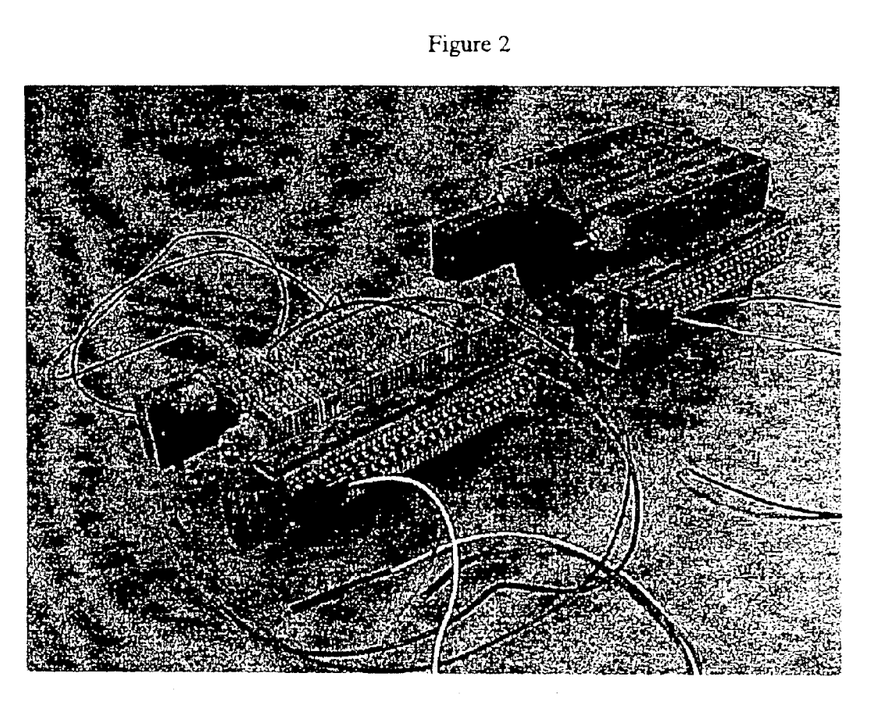
FIG. 2 shows an hourglass electrodynamic funnel and an internal ion funnel built to demonstrate a preferred embodiment of the present invention.

Each metal plate features two pins on opposite sides, supplying the RF and DC potentials from the adjoining electrical connectors. The stack is held together and aligned by four parallel ceramic tubes with bolts inside, and is shown in FIG. 2. The bolts secure the funnel to a plastic (herein peek) disk of the first IMS unit, as described below.

In a regular funnel of prior art, the i.d. of plate holes decreases (or, for certain plates, remains constant) as the ions travel through. In the hourglass funnel disclosed herein, the i.d. decreases over a number of plates (here from 25 mm to 2 mm over 80 plates), then increases (here to ~12 mm over the next 20 plates). The last funnel plate carries only a DC potential (no RF). This plate may be covered with a mesh (here 1 mm. square mesh) to trap ions. In another embodiment, two last plates carry a DC voltage only. As with a regular funnel, an hourglass funnel may feature (in the $1^{st}$ section of decreasing plate holes) a DC-only plate with a jet disrupter for ion intensity control.

Typical DC voltages on the ion source elements for the experiments described herein were (with respect to the IMS entrance potential): ESI needle (~1.3 kV), heated capillary (220 V), first funnel plate (200 V), jet disruptor (175 V), last funnel plate carrying an RF potential (40 V). The potential of last (DC-only) plate is periodically switched between the "closed" state (ions are trapped in the funnel) and "open" state (a packet of ions released into IMS) by a rectangular DC pulse of desired length. Here, the voltages were 30 V and 100 V for open and closed states, respectively.

Figure 3:
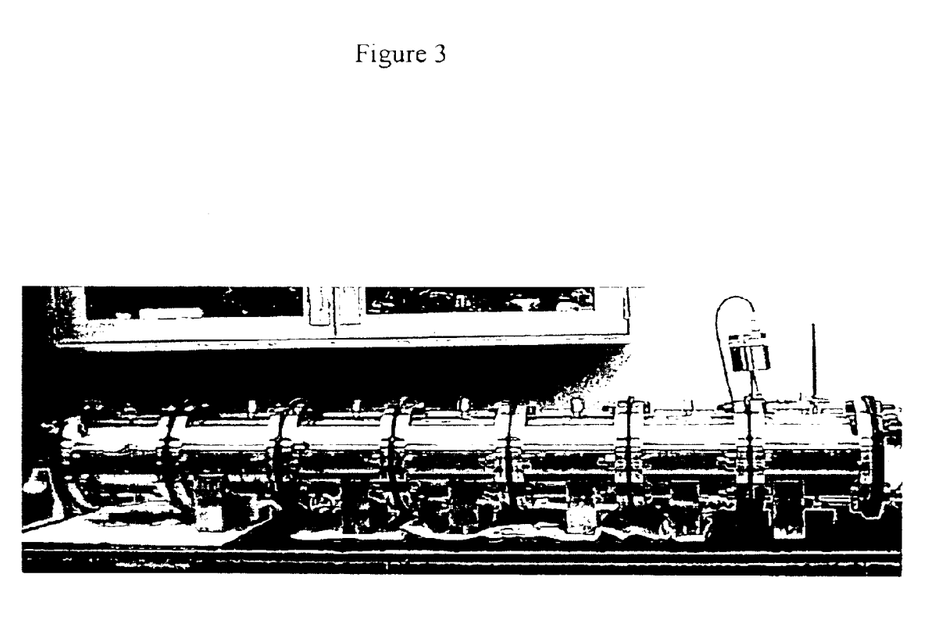
FIG. 3 is a drift tube built to demonstrate a preferred embodiment of the present invention.

As shown in FIG. 3, the drift tube built for these experiments has a modular design, comprising an arbitrary number of nearly-identical units (in this instrument, up to seven). Each unit is housed within a chamber, here a cylindrical steel tube ~20 cm. in diameter and 20 cm. long with wall thickness of ~2 mm. To join the units, each chamber features welded flanges on both ends, here standard 11-inch 8-bolt flanges with O-ring grooves. Some chambers are fit with insulated high-voltage feedthroughs and/or gas lines. Chambers are insulated and spaced apart by plastic (here ultra high molecular weight polyethylene or peek) disks ~1 cm. thick and ~30 cm. in diameter, and fastened by insulating bolts and nuts (here fiberglass-reinforced plastic). These disks have central holes to pass ions between units, and other holes and grooves for electrical connections, alignment, and securing the rods described below.

Each unit includes a stack of thin metal rings (here 21 pieces) positioned and aligned on four parallel ceramic rods (here ~3 mm. in diameter), and insulated and spaced by plastic spacers. Here, rings with the i.d. of ~55 mm and o.d. of ~80 mm are spaced ~10 mm apart. In one embodiment, one or more rings immediately adjacent to the front ED funnel have a smaller i.d. close to the exit funnel diameter (here ~12 mm), which may better collimate the ion packet and improve the ion transmission into the IMS. The assembly is held between two plastic disks by insertion of rods into blind holes in the disks. Rings of any unit are consecutively connected by high-resistance resistors (here 1 MOhm), with same resistances between the units. The median (here $11^{th}$) ring of each unit is electrically shorted to the chamber wall. The first and last rings of the whole tube are connected to outside voltages through feedthroughs.

At the entrance to the drift tube, the ED funnel is mounted on the plastic disk of first unit as described above, so the last funnel plate is ~1 cm. away from the first IMS ring. At the exit to the drift tube, an internal ion funnel is affixed to the plastic disk of last unit. The internal ion funnel is identical to the ED funnel described above, except that it does not exhibit the hourglass shape, contains no jet disruptor, and its mouth is 50 mm in diameter. Voltages applied to the elements of internal ion funnel also mirror those for the ED funnel.

The drift tube contains buffer gas (here He or $N_2$) supplied through lines on the last section. In one embodiment, a cylindrical ring is inserted inside the chamber to let the gas in via a laminar, axially symmetric flow avoiding jet formation and turbulence. The pressure inside is monitored using a capacitance manometer (barotron). In the design built for these experiments, the pressure inside can be varied from 1.5 to 22 Torr using a flow regulator. As will be apparent to those having skill in the art, higher pressures (up to 1 atm) would be attainable with smaller funnel apertures, extra stages of differential pumping, greater pumping capacity in the mass spectrometer (below), or some combination thereof.

The drift voltage was loaded on the first IMS ring by a high-voltage DC power supply with a 50 kV range, monitored by a custom-made HV probe. This supply features a circuit that stabilizes the voltage output, and is current-limited for safety reasons. Other voltages routed to the elements of the ion source are provided by smaller supplies floated on top of the drift voltage. This includes the RF waveform on the ED funnel, supplied by an insulation transformer. The drift voltage is partitioned linearly across the IMS length by the resistor chain described above. The chamber of each unit assumes the voltage of its median ring, thus minimizing the likelihood of electrical breakdown through the gas. To ensure the operator safety, exposed high voltages were contained within a grounded metal cage with controls and interlocks on the access doors.

The The MS analysis of ion packets separated in IMS was performed by a commercial quadrupole time-of-flight mass-spectrometer (Sciex) using a multipole arrangement to transmit ions from exit of the drift tube to the detector. While all commercial mass spectrometers produce mass spectra and therefore may be utilized in conjunction with the present invention, it is important to select one that utilizes an ion transmission means between the drift tube and the detector which does not cause significant delay of the transmission of ions. As used herein, significant delay is defined as less than 5% of total ion drift time in the drift tube. Accordingly, suitable means include, but are not limited to multipole arrangements including quadrupoles, ion tunnels, and ion funnels having a DC gradient down the longitudinal axis to assist ion transmission. For these experiments a standard off the shelf Sciex Q-Star Pulsar instrument was used, as supplied by the manufacturer, with certain modifications. The modificiations include the replacement of the standard curtain gas-orifice-skimmer interface by a custom-built steel chamber that contains a short rf only quadrupole and is differentially pumped by a mechanical pump. This electrically grounded steel chamber is subsequently interfaced with the internal ion funnel as described above. The OEM time-to-digital converter (TDC) was replaced by an Ortec™ TDC which significantly improved performance. In another embodiment, an analog-to-digital (ADC) averager may be substituted for the TDC. This may be beneficial to extend the dynamic range in some regimes, for example at high signal intensities. The manufacturer's software designed for acquisition and processing of mass spectra has no time resolution, and thus was not used with the IMS separation. To record individual ToF spectra along the IMS axis, replacement software was coded, providing the data archival and display in two dimensions. The software is available upon request from the Pacific Northwest National Laboratory operated by Battelle Memorial Institute on behalf of the Department of Energy for use in conjunction with the other described elements of the invention.

An experiment was conducted using the IMS apparatus described above. A sample of Leucine Enkaphalin, at a concentration of 2 pMol/ul, was introduced into the IMS and the ion drift times at different IMS voltages were measured as shown in Table 1.

| IMS Chamber Pressure (Torr) | IMS Voltage (kV) | Drift Time (ms) |
| --- | --- | --- |
| 4.022 | 1.507 | 53.6 |
| 4.004 | 2.005 | 39.6 |
| 4.003 | 3.009 | 26.7 |
| 4.024 | 4.001 | 20.7 |
| 4.02 | 5.000 | 15.9 |

Figure 4:
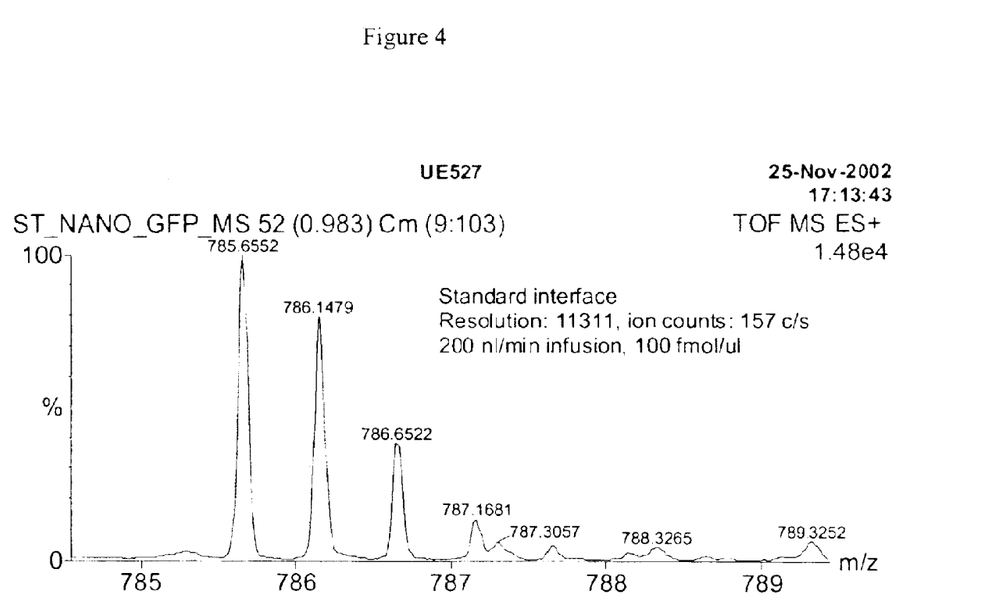
FIG. 4 is a graph showing the ion drift time as inversely proportional to the IMS voltage at a given IMS chamber pressure for a series of experiments conducted with a preferred embodiment of the present invention.
Figure 5:
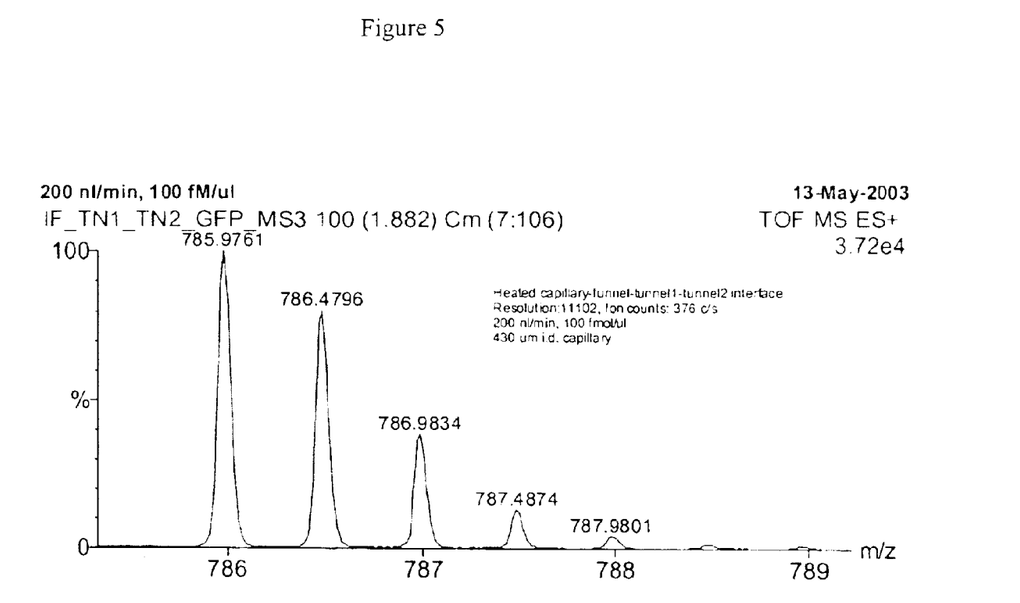
FIG. 5 is a mass-spectrum of Glu-Fibrinopeptide (1572 amu) from a commercial (prior art) Micromass system.
Figure 6:
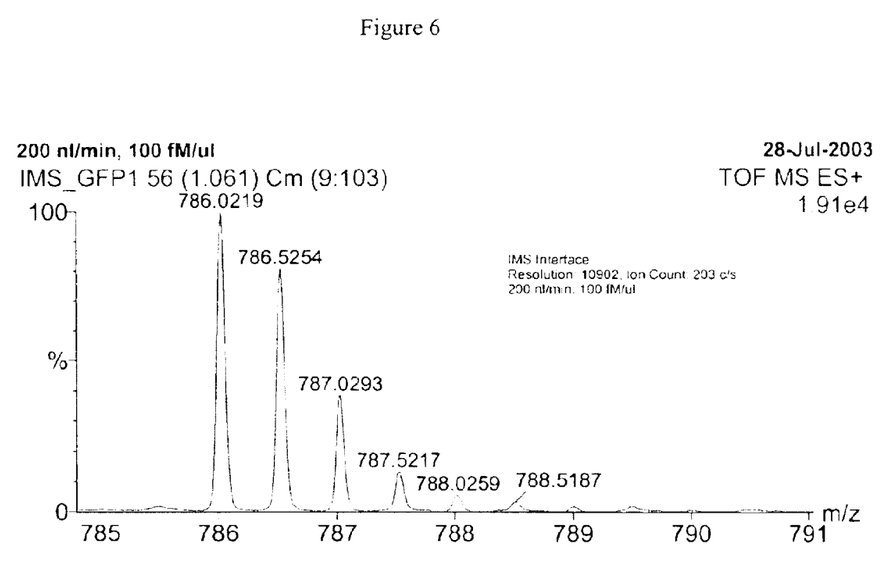
FIG. 6 is a mass-spectrum of Glu-Fibrinopeptide (1572 amu) from a commercial (prior art) Micromass system fitted with a standard ion funnel at the ESI/MS interface.
Figure 7:
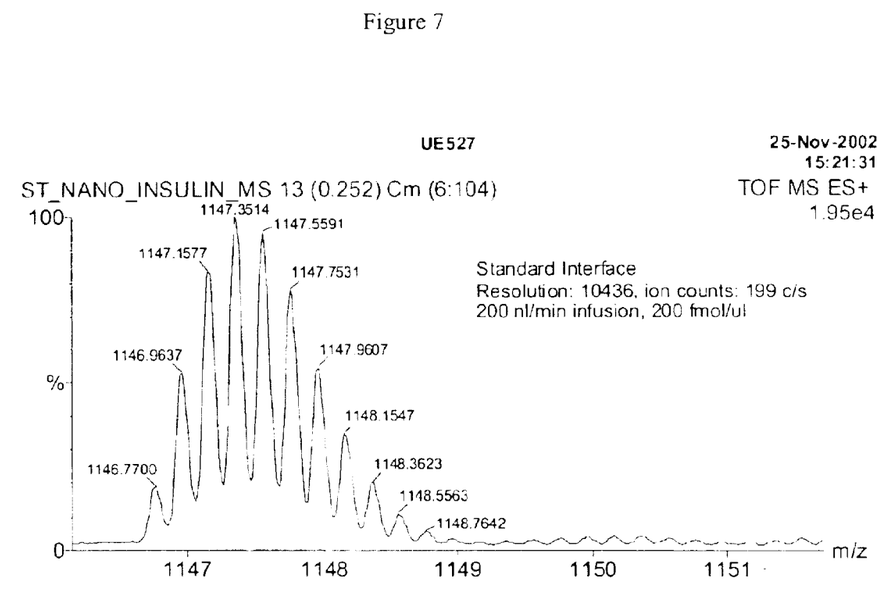
FIG. 7 is a mass-spectrum of Glu-Fibrinopeptide (1572 amu) passed through the hourglass electrodynamic funnel, the IMS drift tube, and the internal ion funnel described in the preferred embodiment of the present invention.
Figure 8:
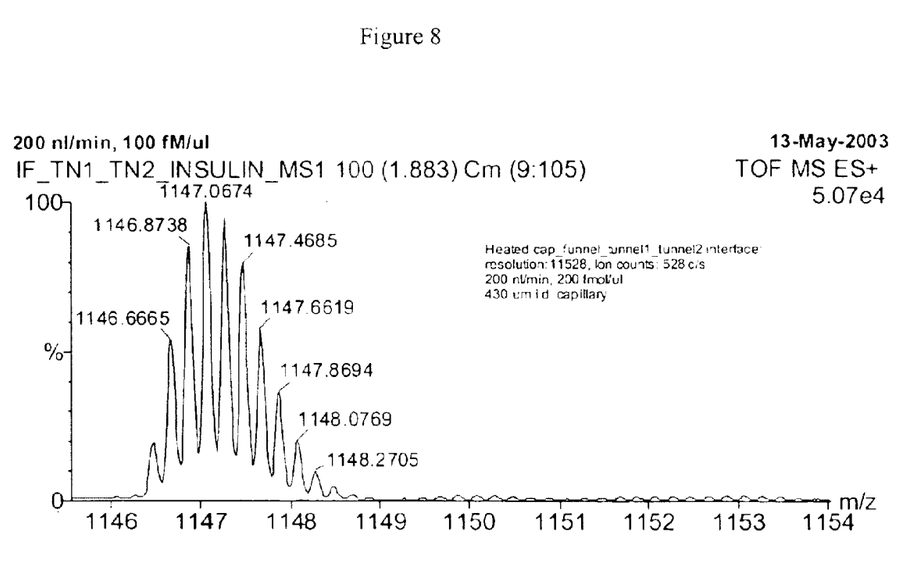
FIG. 8 is a mass-spectrum of Insulin (5734 amu) from a commercial (prior art) Micromass system
Figure 9:
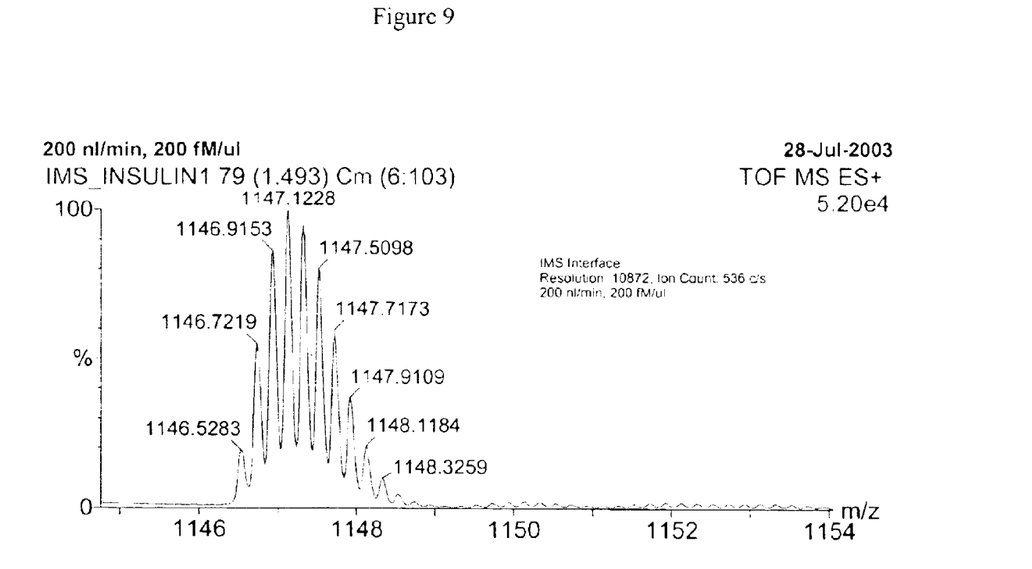
FIG. 9 is a mass-spectrum of Insulin (5734 amu) from a commercial (prior art) Micromass system fitted with a standard ion funnel at the ESI/MS interface.
Figure 10:
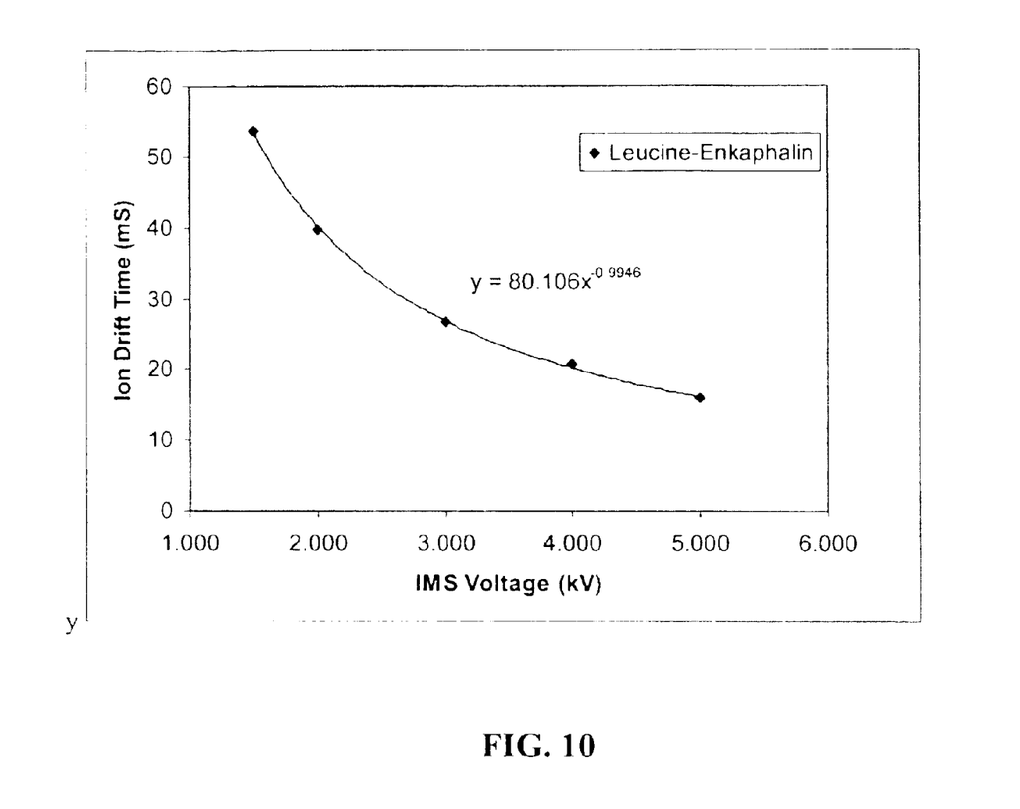
FIG. 10 is a mass-spectrum of Insulin (5734 amu) passed through the hourglass electrodynamic ion funnel, the IMS drift tube, and the internal ion funnel described in the preferred embodiment of the present invention.

Consistent with the ion mobility theory, the experimental data shown in FIG. 4 indicate that ion drift time is inversely proportional to the IMS voltage at a given IMS chamber pressure.

The embodiment described in the parent case was operated to generate the mass-spectra shown in FIGS. 5–10. These systematically compare the signal intensity in the commercial system, the commercial system fitted with a standard (non-hourglass) ED funnel upfront, and the IMS/MS setup. As shown in the spectra, the embodiment achieved exceptional ion transmission efficiency. The comparison is made for two peptide ions—a relatively small (Glu-Fibrinopeptide, 1572 amu) and large (Insulin, 5734 amu) that roughly bracket the range of peptide masses relevant to routine proteomic analyses. The ESI operational conditions (noted on the spectra) are typical for calibration protocols standard in the bioanalytical applications industry. For both peptides, the signal intensity in present IMS/MS arrangement is within a factor of two of that for MS analysis only (without IMS). This is an accepted variance due to day-to-day (random) variations in poorly controlled ESI source conditions on the same instrument. Hence, within the error margin normal for such calibrations, there is essentially no measurable ion loss in the IMS stage.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. An apparatus useful for gas phase analysis of ions comprising:
   a. An hourglass electrodynamic funnel formed of at least an entry element, a center element, and an exit element, each of said elements having an aperture, and wherein said entry element is aligned such that a passageway for charged particles is formed through the aperture within said entry element, through the aperture in said center element, and then through the aperture in said exit element, and wherein said aperture in said center element is smaller than the aperture of said entry and said exit elements;
   b. a drift tube, wherein the hourglass electrodynamic funnel forms the entrance to the drift tube thereby providing a passageway for ions generated in a relatively high pressure region at the exterior of the drift tube to a relatively low pressure region at the interior of the drift tube through said elements;
   c. a detector having a ion transmission means for transmitting ions from the exit of said drift tube to a time-of-flight detector wherein said ion transmission means allows the transmission of ions at less than 5% of the total ion drift time in said ion drift tube.

2. The apparatus of claim 1 further comprising a jet disturber placed within said hourglass electrodynamic funnel.

3. The apparatus of claim 1 wherein said apertures have a shape selected from the group consisting of circular, ellipsoidal, and rectangular.

4. The apparatus of claim 1 further comprising a means for temporarily containing the flow of ions out of the aperture of said exit element of said hourglass electrodynamic funnel.

5. The apparatus of claim 4 wherein said means is selected from the group consisting of a plurality of wires, a mesh, and a microchannel plate.

6. The apparatus of claim 1 further comprising a means for intermittently terminating the flow of ions by deflecting them using an electric field orthogonal to the ion path.

7. The apparatus of claim 6 wherein said means is selected from the group consisting of a Bradbury-Nielsen gate, two or more deflection plates, and a split lens.

8. The apparatus of claim 1 further comprising an ion analysis means in communication with an exit to said drift tube, said exit located at the opposite end of said drift tube from said electrodynamic funnel.

9. The apparatus of claim 8 wherein said ion analysis means is selected from the group consisting of a mass spectrometer, a photoelectron spectrometer, and a photodissociation spectrometer.

10. The apparatus of claim 9 wherein said mass spectrometer is selected from the group consisting of a quadrupole mass spectrometer, a time of flight mass spectrometer, and a Fourier-transform ion cyclotron resonance mass spectrometer.

11. The apparatus of claim 1 wherein said drift tube is an ion mobility spectrometer.

12. The apparatus of claim 1 wherein said drift tube is selected from the group consisting of a field asymmetric waveform ion mobility spectrometer, a selected ion flow tube, and a proton-transfer reaction mass spectrometer.

13. The apparatus of claim 1 further comprising a means for generating ions in communication with said entry element.

14. The apparatus of claim 13 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

15. The apparatus of claim 1 further comprising an internal ion funnel having at least one element having a relatively small aperture and at least one element having a relatively large aperture positioned at the exit of said drift tube wherein the element having the small aperture is positioned adjacent to the exit of said drift tube.

16. The apparatus of claim 1 further comprising a second hourglass electrodynamic funnel also formed of at least an entry element, a center element, and an exit element, each of said elements having an aperture, wherein said entry element is aligned such that a second passageway for charged particles is formed through the aperture within said entry element, through the aperture in said center element and through the aperture in said exit element, and wherein said aperture in said center element is smaller than the aperture of said entry and said exit elements, and wherein the second hourglass electrodynamic funnel forms a separate entrance to the drift tube thereby providing a second passageway for ions generated in a relatively high pressure region at the exterior of the drift tube to a relatively low pressure region at the interior of the drift tube.

17. The apparatus of claim 16 further comprising a jet disturber placed within at least one of said hourglass electrodynamic funnels.

18. The apparatus of claim 16 wherein said apertures have a shape selected from the group consisting of circular, ellipsoidal, rectangular, and combinations thereof.

19. The apparatus of claim 16 further comprising a means for temporarily containing the flow of ions out of the aperture of at least one of said exit elements of said hourglass electrodynamic funnels.

20. The apparatus of claim 19 wherein said means is selected from the group consisting of a plurality of wires, a mesh, and a microchannel plate.

21. The apparatus of claim 16 further comprising a means for intermittently terminating the flow of ions by deflecting them using an electric field orthogonal to the ion path.

22. The apparatus of claim 21 wherein said means is selected from the group consisting of a Bradbury-Nielsen gate, two or more deflection plates, and a split lens.

23. The apparatus of claim 16 further comprising an ion analysis means in communication with an exit to said drift tube, said exit located at the opposite end of said drift tube from said electrodynamic funnel.

24. The apparatus of claim 23 wherein said ion analysis means is selected from the group consisting of a mass spectrometer, a photoelectron spectrometer, and a photodissociation spectrometer.

25. The apparatus of claim 24 wherein said mass spectrometer is selected from the group consisting of a quadrupole mass spectrometer, a time of flight mass spectrometer, and a Fourier-transform ion cyclotron resonance mass spectrometer.

26. The apparatus of claim 16 wherein said drift tube is an ion mobility spectrometer.

27. The apparatus of claim 16 wherein said drift tube is selected from the group consisting of a field asymmetric waveform ion mobility spectrometer, a selected ion flow tube, and a proton-transfer reaction mass spectrometer.

28. The apparatus of claim 16 further comprising a means for generating ions in communication with at least one of said entry elements.

29. The apparatus of claim 28 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

30. The apparatus of claim 16 further comprising an internal ion funnel having at least one element having a relatively small aperture and at least one element having a relatively large aperture positioned at the exit of said drift tube wherein the element having the small aperture is positioned adjacent to the exit of said drift tube.

31. An apparatus useful for gas phase analysis of ions comprising:
   a. An dual entry hourglass electrodynamic funnel formed of at least two entry elements, one center element, and one exit element, each of said elements having an aperture, and wherein each of said two entry elements are aligned such that a passageway for charged particles is formed through apertures within said entry elements, through the aperture in said center element and through the aperture in said exit element, and wherein said aperture in said center element is smaller than the aperture of said entry and said exit element;
   b. a drift tube, wherein the dual source hourglass electrodynamic funnel forms the entrance to the drift tube thereby providing two separate but merging passageways for ions generated in a relatively high pressure region at the exterior of the drift tube to a relatively low pressure region at the interior of the drift tube; and
   c. A detector having a ion transmission means for transmitting ions from the exit of said drift tube to a time-of-flight detector wherein said ion transmission means allows the transmission of ions at less than 5% of the total ion drift time in said ion drift tube.

32. The apparatus of claim 31 further comprising a jet disturber placed within said dual source hourglass electrodynamic funnel.

33. The apparatus of claim 31 wherein said apertures have a shape selected from the group consisting of circular, ellipsoidal, and rectangular.

34. The apparatus of claim 31 further comprising a means for temporarily containing the flow of ions out of the aperture of said exit element of said dual source hourglass electrodynamic funnel.

35. The apparatus of claim 34 wherein said means is selected from the group consisting of a plurality of wires, a mesh, and a microchannel plate.

36. The apparatus of claim 31 further comprising a means for intermittently terminating the flow of ions by deflecting them using an electric field orthogonal to the ion path.

37. The apparatus of claim 36 wherein said means is selected from the group consisting of a Bradbury-Nielsen gate, two or more deflection plates, and a split lens.

38. The apparatus of claim 31 further comprising an ion analysis means in communication with an exit to said drift tube, said exit located at the opposite end of said drift tube from said electrodynamic funnel.

39. The apparatus of claim 38 wherein said ion analysis means is selected from the group consisting of a mass spectrometer, a photoelectron spectrometer, and a photodissociation spectrometer.

40. The apparatus of claim 39 wherein said mass spectrometer is selected from the group consisting of a quadrupole mass spectrometer, a time of flight mass spectrometer, and a Fourier-transform ion cyclotron resonance mass spectrometer.

41. The apparatus of claim 31 wherein said drift tube is an ion mobility spectrometer.

42. The apparatus of claim 31 wherein said drift tube is selected from the group consisting of a field asymmetric waveform ion mobility spectrometer, a selected ion flow tube, and a proton-transfer reaction mass spectrometer.

43. The apparatus of claim 31 further comprising a means for generating ions for in communication with said entry element.

44. The apparatus of claim 43 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

45. The apparatus of claim 31 further comprising an ion detection means wherein said ion detection means is configured to received ions exiting from said drift tube from the end of said drift tube opposite said dual source hourglass electrodynamic funnel.

46. A method for gas phase analysis of ions comprising the steps of:
   a. providing an hourglass electrodynamic funnel formed of at least an entry element, a center element, and an exit element, each of said elements having an aperture, and wherein said entry element is aligned such that a passageway for charged particles is formed through the aperture within said entry element, through the aperture in said center element, and then through the aperture in said exit element, and wherein said aperture in said center element is smaller than the aperture of said entry and said exit elements;
   b. providing a drift tube, wherein the hourglass electrodynamic funnel forms the entrance to the drift tube thereby providing a passageway for ions generated in a relatively high pressure region at the exterior of the drift tube to a relatively low pressure region at the interior of the drift tube through said elements;
   c. introducing ions into said entry element; and
   d. providing a detector having a ion transmission means for transmitting ions from the exit of said drift tube to a time-of-flight detector wherein said ion transmission means allows the transmission of ions at less than 5% of the total ion drift time in said ion drift tube.

47. The method of claim 46 further comprising the step of providing a jet disturber placed within said hourglass electrodynamic funnel.

48. The method of claim 46 wherein said apertures are provided as having a shape selected from the group consisting of circular, ellipsoidal, and rectangular.

49. The method of claim 46 further comprising providing a means for temporarily containing the flow of ions out of the aperture of said exit element of said hourglass electrodynamic funnel thereby allowing groups of ions to pass from said exit element at a known time.

50. The method of claim 49 wherein said means is selected from the group consisting of a plurality of wires, a mesh, and a microchannel plate, and intermittently applying an electrical potential to said means, thereby allowing groups of ions to pass from said exit element at a known time.

51. The method of claim 46 further comprising the step of providing a means for intermittently terminating the flow of ions by deflecting them using an electric field orthogonal to the ion path.

52. The method of claim 51 wherein said means is provided as selected from the group consisting of a Bradbury-Nielsen gate, two or more deflection plates, and a split lens.

53. The method of claim 46 further comprising the step of providing an ion analysis means in communication with an exit to said drift tube, said exit located at the opposite end of said drift tube from said electrodynamic funnel.

54. The method of claim 53 wherein said ion analysis means is selected from the group consisting of a mass spectrometer, a photoelectron spectrometer, and a photodissociation spectrometer.

55. The method of claim 54 wherein said mass spectrometer is selected from the group consisting of a quadrupole mass spectrometer, a time of flight mass spectrometer, and a Fourier-transform ion cyclotron resonance mass spectrometer.

56. The method of claim 46 wherein said drift tube is provided as an ion mobility spectrometer.

57. The method of claim 46 wherein said drift tube is selected from the group consisting of a field asymmetric waveform ion mobility spectrometer, a selected ion flow tube, and a proton-transfer reaction mass spectrometer.

58. The method of claim 46 further comprising providing a means for generating ions in communication with said entry element.

59. The method of claim 58 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

60. The method of claim 46 further comprising the step of providing an internal ion funnel having at least one element having a relatively small aperture and at least one element having a relatively large aperture positioned at the exit of said drift tube wherein the element having the small aperture is positioned adjacent to the exit of said drift tube.

61. The method of claim 46 further comprising the steps of
   a. providing a second hourglass electrodynamic funnel also formed of at least an entry element, a center element, and an exit element, each of said elements having an aperture, wherein said entry element is aligned such that a second passageway for charged particles is formed through the aperture within said entry element, through the aperture in said center element and through the aperture in said exit element, and wherein said aperture in said center element is smaller than the aperture of said entry and said exit elements, and wherein the second hourglass electrodynamic funnel forms a separate entrance to the drift tube thereby providing a second passageway for ions generated in a relatively high pressure region at the exterior of the drift tube to a relatively low pressure region at the interior of the drift tube and
   b. introducing ions through said entry element of said second electrodynamic funnel.

62. The method of claim 61 further comprising the step of providing a jet disturber placed within at least one of said hourglass electrodynamic funnels.

63. The method of claim 61 wherein said apertures have a shape selected from the group consisting of circular, ellipsoidal, rectangular, and combinations thereof.

64. The method of claim 61 further comprising the step of providing a means for temporarily containing the flow of ions out of the aperture of at least one of said exit elements of said hourglass electrodynamic funnels thereby allowing groups of ions to pass from said exit element at a known time.

65. The method of claim 64 wherein said means is selected from the group consisting of a plurality of wires, a mesh, and a microchannel plate, and intermittently applying an electrical potential to said means, thereby allowing groups of ions to pass from said exit element at a known time.

66. The method of claim 61 further comprising the step of providing a means for terminating the flow of ions by deflecting them using an electric field orthogonal to the ion path.

67. The method of claim 66 wherein said means is provided as selected from the group consisting of a Bradbury-Nielsen gate, two or more deflection plates, and a split lens.

68. The method of claim 61 further comprising the step of providing an ion analysis means in communication with an exit to said drift tube, said exit located at the opposite end of said drift tube from said electrodynamic funnel.

69. The method of claim 68 wherein said ion analysis means is selected from the group consisting of a mass spectrometer, a photoelectron spectrometer, and a photodissociation spectrometer.

70. The method of claim 69 wherein said mass spectrometer is provided as selected from the group consisting of a quadrupole mass spectrometer, a time of flight mass spectrometer, and a Fourier-transform ion cyclotron resonance mass spectrometer.

71. The method of claim 61 wherein said drift tube is provided as an ion mobility spectrometer.

72. The method of claim 61 wherein said drift tube is selected from the group consisting of a field asymmetric waveform ion mobility spectrometer, a selected ion flow tube, and a proton-transfer reaction mass spectrometer.

73. The method of claim 61 further comprising the step of providing a means for generating ions for in communication with at least one of said entry elements.

74. The method of claim 73 wherein said means for generating ions is provided as selected from the group consisting of electrospray ionization, coldspray ionization, thermospray ionization, matrix-assisted laser desorption ionization, surface-enhanced laser desorption ionization, laser vaporization, and arc discharge.

75. The method of claim 61 further comprising the step of providing an internal ion funnel having at least one element having a relatively small aperture and at least one element having a relatively large aperture positioned at the exit of said drift tube wherein the element having the small aperture is positioned adjacent to the exit of said drift tube.

76. An method for gas phase analysis of ions comprising the steps of:
   a. providing an dual entry hourglass electrodynamic funnel formed of at least two entry elements, one center element, and one exit element, each of said elements having an aperture, and wherein each of said two entry elements are aligned such that a passageway for charged particles is formed through apertures within said entry elements, through the aperture in said center element and through the aperture in said exit element, and wherein said aperture in said center element is smaller than the aperture of said entry and said exit element;
   b. providing a drift tube, wherein the dual source hourglass electrodynamic funnel forms the entrance to the drift tube thereby providing two separate but merging passageways for ions generated in a relatively high pressure region at the exterior of the drift tube to a relatively low pressure region at the interior of the drift tube;
   c. introducing ions into the aperture of at least one of said entry elements; and
   d. providing a detector having a ion transmission means for transmitting ions from the exit of said drift tube to a time-of-flight detector wherein said ion transmission means allows the transmission of ions at less than 5% of the total ion drift time in said ion drift tube.

77. The method of claim 76 further comprising the step of providing a jet disturber placed within said dual source hourglass electrodynamic funnel.

78. The method of claim 76 wherein said apertures have a shape selected from the group consisting of circular, ellipsoidal, and rectangular.

79. The method of claim 76 further comprising a means for temporarily containing the flow of ions out of the aperture of said exit element of said dual source hourglass electrodynamic funnel.

80. The method of claim 79 wherein providing said means is selected from the group consisting of a plurality of wires, a mesh, and a microchannel plate and intermittently applying an electrical potential to said means, thereby allowing groups of ions to pass from said exit element at a known time.

81. The method of claim 76 further comprising the step of providing a means for intermittently terminating the flow of ions by deflecting them using an electric field orthogonal to the ion path.

82. The method of claim 81 wherein said means is provided as selected from the group consisting of a Bradbury-Nielsen gate, two or more deflection plates, and a split lens.

83. The method of claim 76 further comprising the step of providing an ion analysis means in communication with an exit to said drift tube, said exit located at the opposite end of said drift tube from said electrodynamic funnel.

84. The method of claim 83 wherein said ion analysis means is selected from the group consisting of a mass spectrometer, a photoelectron spectrometer, and a photodissociation spectrometer.

85. The method of claim 84 wherein said mass spectrometer is selected from the group consisting of a quadrupole mass spectrometer, a time of flight mass spectrometer, and a Fourier-transform ion cyclotron resonance mass spectrometer.

86. The method of claim 76 wherein said drift tube is an ion mobility spectrometer.

87. The method of claim 76 wherein said drift tube is selected from the group consisting of a field asymmetric waveform ion mobility spectrometer, a selected ion flow tube, and a proton-transfer reaction mass spectrometer.

88. The method of claim 76 further comprising the step of providing a means for generating ions for in communication with said entry element.

89. The method of claim 88 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

90. The method of claim 76 further comprising the step of providing an ion detection means wherein said ion detection means is configured to receive ions exiting from said drift tube from the end of said drift tube opposite said dual source hourglass electrodynamic funnel.

91. An method for gas phase analysis of ions comprising the steps of:
   a. providing a drift tube having an internal ion funnel having at least one element having a relatively small aperture and at least one element having a relatively large aperture positioned at the exit of said drift tube and wherein the element having the small aperture is positioned to transfer ions from inside of said drift tube out of the exit of said drift tube;
   b. providing ions into an entry to said drift tube at the end opposite to said ion funnel; and
   c. providing a detector having a ion transmission means for transmitting ions from the exit of said drift tube to a time-of-flight detector wherein said ion transmission means allows the transmission of ions at less than 5% of the total ion drift time in said ion drift tube.

92. The method of claim 91 further comprising the step of providing a jet disturber placed within said internal ion funnel.

93. The method of claim 91 wherein said apertures have a shape selected from the group consisting of circular, ellipsoidal, and rectangular.

94. The method of claim 91 further comprising the step of providing a means for temporarily containing the flow of ions out of the aperture of said one element having a relatively small aperture of said internal ion funnel.

95. The method of claim 91 wherein said means is provided as selected from the group consisting of a plurality of wires, a mesh, and a microchannel plate and intermittently applying an electrical potential to said means, thereby allowing groups of ions to pass from said exit element at a known time.

96. The method of claim 91 further comprising the step of providing a means for intermittently terminating the flow of ions by deflecting them using an electric field orthogonal to the ion path.

97. The method of claim 96 wherein said means is provided as selected from the group consisting of a Bradbury-Nielsen gate, two or more deflection plates, and a split lens.

98. The method of claim 91 further comprising the step of providing an ion analysis means in communication with said exit to said drift tube.

99. The method of claim 91 wherein said ion analysis means is selected from the group consisting of a mass spectrometer, a photoelectron spectrometer, and a photodissociation spectrometer.

100. The method of claim 99 wherein said mass spectrometer is selected from the group consisting of a quadrupole mass spectrometer, a time of flight mass spectrometer, and a Fourier-transform ion cyclotron resonance mass spectrometer.

101. The method of claim 91 comprising the further step of providing said drift tube as an ion mobility spectrometer.

102. The method of claim 91 wherein said drift tube is selected from the group consisting of a field asymmetric waveform ion mobility spectrometer, a selected ion flow tube, and a proton-transfer reaction mass spectrometer.

103. The method of claim 91 further comprising the step of providing a means for generating ions for in communication with an entry to said drift tube at the opposite end of said drift tube as said internal ion funnel.

104. The method of claim 103 wherein said means for generating ions is selected from the group consisting of electrospray ionization, coldspray ionization, thermospray ionization, matrix-assisted laser desorption ionization, surface-enhanced laser desorption ionization, laser vaporization, and arc discharge.

* * * * *